(12) United States Patent
Kantrowitz et al.

(10) Patent No.: US 7,683,781 B2
(45) Date of Patent: Mar. 23, 2010

(54) AUTO ID SYSTEM FOR MEDICAL CARE SETTING

(76) Inventors: Allen B. Kantrowitz, 190 Torrey Woods Rd., Williamstown, MA (US) 01267; In K. Mun, 1 Apple Ct., Nanuet, NY (US) 10958

( * ) Notice: Subject to any disclaimer, the term of this patent is extended or adjusted under 35 U.S.C. 154(b) by 223 days.

(21) Appl. No.: 11/488,320

(22) Filed: Jul. 18, 2006

(65) Prior Publication Data
US 2007/0013528 A1   Jan. 18, 2007

Related U.S. Application Data

(60) Provisional application No. 60/700,126, filed on Jul. 18, 2005.

(51) Int. Cl.
*G08B 13/14* (2006.01)
(52) U.S. Cl. ............ 340/572.1; 340/572.4; 340/10.1; 726/5
(58) Field of Classification Search ............ 340/572.1, 340/10.1, 572.4; 726/5
See application file for complete search history.

(56) References Cited

U.S. PATENT DOCUMENTS

| | | | |
|---|---|---|---|
| 5,963,136 A | 10/1999 | O'Brien | |
| 5,973,600 A | 10/1999 | Mosher, Jr. | |
| 6,111,506 A * | 8/2000 | Yap et al. ............ | 340/572.1 |
| 6,150,942 A | 11/2000 | O'Brien | |
| 6,215,403 B1 | 4/2001 | Chan et al. | |
| 6,375,038 B1 | 4/2002 | Daansen et al. | |
| 6,577,240 B2 | 6/2003 | Armstrong | |
| 6,624,752 B2 | 9/2003 | Klitsgaard et al. | |
| 6,753,782 B2 | 6/2004 | Power et al. | |
| 6,753,783 B2 | 6/2004 | Friedman et al. | |
| 6,774,782 B2 | 8/2004 | Runyon et al. | |
| 6,853,303 B2 | 2/2005 | Chen et al. | |
| 6,937,154 B2 | 8/2005 | Zeps et al. | |
| 6,954,148 B2 | 10/2005 | Pulkkinen et al. | |
| 6,983,884 B2 | 1/2006 | Auchinleck | |
| 6,989,741 B2 * | 1/2006 | Kenny et al. ............ | 340/505 |
| 6,998,978 B2 | 2/2006 | Kirkeby | |
| 7,002,476 B2 | 2/2006 | Rapchak | |
| 7,106,189 B2 | 9/2006 | Burneske et al. | |

(Continued)

FOREIGN PATENT DOCUMENTS

TW    243345 B    11/2005

*Primary Examiner*—Toan N Pham
*Assistant Examiner*—Kerri McNally
(74) *Attorney, Agent, or Firm*—Avery N. Goldstein

(57) ABSTRACT

A system for verifying patient identity is detailed which allows hospital personnel to reduce error in patient care due to misidentification of a patient. Broadly, an inventive system for verifying patient identity includes a machine readable wireless identification tag containing identification information, the tag attached to an identification badge worn by a patient, a device having data input and output capacity, processing circuitry, memory circuitry and an executable program for analysis of data transmitted from the tag, and a machine wireless reader in data communication with the tag and the device. Also included is a signal display element for displaying a signal to a user, the signal display element disposed on the device or the reader. Further, an alert system is provided for alerting hospital personnel to presence of an object or person having a machine readable wireless tag not associated with a first patient in proximity to the first patient.

9 Claims, 2 Drawing Sheets

U.S. PATENT DOCUMENTS

| | | |
|---|---|---|
| 7,154,397 B2 | 12/2006 | Zerhusen et al. |
| 7,155,202 B2 | 12/2006 | Helal |
| 7,161,484 B2 | 1/2007 | Tsoukalis et al. |
| 7,198,190 B2 | 4/2007 | Juhan et al. |
| 7,218,232 B2 | 5/2007 | DiSilvestro et al. |
| 7,221,276 B2 * | 5/2007 | Olsen et al. .............. 340/572.1 |
| 2001/0028308 A1 | 10/2001 | De La Huerga |
| 2002/0017996 A1 | 2/2002 | Niemiec |
| 2002/0017998 A1 | 2/2002 | Price |
| 2002/0044059 A1 | 4/2002 | Reeder et al. |
| 2002/0080034 A1 | 6/2002 | Yahalom |
| 2002/0145526 A1 | 10/2002 | Friedman et al. |
| 2002/0196150 A1 | 12/2002 | Wildman |
| 2003/0016122 A1 | 1/2003 | Petrick |
| 2003/0043040 A1 | 3/2003 | Zeps et al. |
| 2003/0052787 A1 | 3/2003 | Zerhusen et al. |
| 2003/0052788 A1 | 3/2003 | Kwong-Tai Chung |
| 2003/0067386 A1 | 4/2003 | Skinner |
| 2003/0071734 A1 | 4/2003 | Vodin |
| 2003/0160698 A1 | 8/2003 | Andreasson et al. |
| 2003/0227386 A1 | 12/2003 | Pulkkinen et al. |
| 2004/0100376 A1 | 5/2004 | Lye et al. |
| 2004/0150525 A1 | 8/2004 | Wilson et al. |
| 2004/0155780 A1 | 8/2004 | Rapchak |
| 2004/0249250 A1 | 12/2004 | McGee et al. |
| 2005/0009191 A1 * | 1/2005 | Swenson et al. .............. 436/43 |
| 2005/0035862 A1 | 2/2005 | Wildman et al. |
| 2005/0073419 A1 | 4/2005 | Gary |
| 2005/0088306 A1 | 4/2005 | Andreasson et al. |
| 2005/0093709 A1 | 5/2005 | Franco et al. |
| 2005/0110640 A1 * | 5/2005 | Chung .................... 340/572.1 |
| 2005/0151640 A1 | 7/2005 | Hastings |
| 2005/0231373 A1 | 10/2005 | Lynn et al. |
| 2005/0242928 A1 | 11/2005 | Kirkeby |
| 2005/0280536 A1 | 12/2005 | Hamilton et al. |
| 2006/0001545 A1 | 1/2006 | Wolf |
| 2006/0033625 A1 | 2/2006 | Johnson et al. |
| 2006/0066450 A1 | 3/2006 | Jackson |
| 2006/0145876 A1 | 7/2006 | Kimura et al. |
| 2006/0218626 A1 * | 9/2006 | Goehler ........................ 726/5 |
| 2006/0244592 A1 * | 11/2006 | Kansala et al. ............. 340/571 |
| 2006/0267753 A1 * | 11/2006 | Hussey et al. .............. 340/505 |
| 2006/0279427 A1 | 12/2006 | Becker et al. |
| 2006/0290519 A1 | 12/2006 | Boate et al. |
| 2007/0008149 A1 | 1/2007 | Bolling |
| 2007/0024453 A1 | 2/2007 | Mohammed et al. |
| 2007/0040692 A1 | 2/2007 | Smith et al. |
| 2007/0046476 A1 | 3/2007 | Hinkamp |
| 2007/0085690 A1 | 4/2007 | Tran |

* cited by examiner

US 7,683,781 B2

AUTO ID SYSTEM FOR MEDICAL CARE SETTING

RELATED APPLICATION

This application claims priority of U.S. Provisional Patent Application Ser. No. 60/700,126 filed Jul. 18, 2005, which is incorporated herein by reference.

FIELD OF THE INVENTION

The invention relates to management of patient care and systems and methods designed for use in minimizing mistaken treatment of the wrong patient. In particular, the invention relates to systems and methods for verification of patient identity and alerting hospital personnel to presence of items not intended for care of the patient.

BACKGROUND OF THE INVENTION

Patient care becomes increasingly complex as hospitals increase capacity to treat individuals in both outpatient and inpatient settings. In particular, due to the large number of patients, staff and medical personnel, it is increasingly common for a patient to receive care from successive teams of caregivers, rather than a single individual or a group who follow the patient's treatment each day. A consequence of the greater number of patients and hospital personnel is an increase in the probability of error due to misidentification of the patient. Previous methods of verifying the identity of a patient in a treatment setting included visual inspection of an identity badge such as a wristband with written indicia. Similarly, in administering a drug or other treatment, the container is typically labeled with written indicia signifying the intended patient. Such methods are always subject to difficulties such as illegibility, destruction, loss and misassociation of such labels, potentially resulting in incorrect treatment of the patient.

Thus, an improved system and process for positively identifying a patient is needed. Further, an improved system and process for alerting medical care personnel to the presence of a person or object not associated with the patient is needed.

SUMMARY OF THE INVENTION

A system for verifying patient identity is provided which includes an identification badge to be worn by a patient or attached to clothing worn by the patient. An included identification badge has an attached machine readable wireless tag which contains identification information. In a preferred option the identification badge is a wristband attached to the patient.

An inventive system includes a device having data input and output capacity, processing circuitry, memory circuitry and an executable program for analysis of data transmitted from the tag. Further included is a machine readable wireless reader in data communication with the tag and the device, and a signal display indicator disposed on the reader or the device. The signal display indicator is operative to display a first signal, such as a signal indicative of a pending process, or verified or non-verified patient identity, in response to a command by the executable program. The signal display indicator displays a first signal which is a visual signal and an acoustic signal such as provided by a light or sound source.

Optionally, the signal display indicator is operative to present a second signal. In a further option, a status indicator is included attached to the identification badge. The status indicator is operative to present a first cue in response to a command by the executable program, such as a signal indicative of a pending process, or verified or non-verified patient identity. The first cue is a visual and/or acoustic cue such as provided by a light or sound source.

An inventive system further optionally includes a power source attached to an RFID badge. The power source may be in electrical communication with the status indicator. Further optionally, a power source may be in electrical communication with the tag.

In one embodiment, a device is provided having data input and output capacity, processing circuitry, memory circuitry and a program executable by the processing circuitry and memory circuitry to compare identification information transmitted to the tag with identification information contained in the tag to determine whether the transmitted identification information matches the identification information contained in the tag and to activate a status indicator to present a cue indicative of a match or a mismatch between the transmitted identification information and the identification information contained in the tag.

Also provided is a system for alerting hospital personnel to presence of an object or person having a radio frequency identification tag not associated with a first patient in proximity to the first patient. The system includes a first radio frequency tag containing identification information associated with a first patient, the tag attached to an object associated with the target patient. Also included is a second machine readable wireless tag containing identification information specific to a second patient, the tag attached to an object associated with the second patient and not associated with the first patient. Further, a device is provided having data input and output capacity, processing circuitry, memory circuitry and an executable program for analysis of data transmitted from the first tag and the second tag. A machine readable wireless reader is included in data communication with the first tag, the second tag, and the device. Also included is a signal display indicator in data communication with the device.

Exemplary objects which may be associated with the first patient include an identification badge, a medication container, a specimen container and a specimen preparation, such as a slide. In addition, a meal tray having foods identified as acceptable for the first patient may be associated with the first patient. Optionally, an item of medical equipment, such a cannula, stent, valve or joint replacement part and the like, destined for use in treatment of the first patient may be associated with the patient as described herein. Similarly, such objects may be associated with a second patient.

In one option, the reader is in a fixed location in proximity to the first patient. An inventive system may further include a second radio frequency identification reader in a fixed location in proximity to the second patient.

Optionally, first tag and the second tag included in an inventive system are selected from the group consisting of: passive RFID or barcodes, active, read-only and read-write. In a further option, the device is selected from the group consisting of: a personal digital assistant, a personal computer a mainframe and a server. Additionally, in one embodiment, the reader may be disposed on the device.

DETAILED DESCRIPTION OF THE INVENTION

Figure 1:
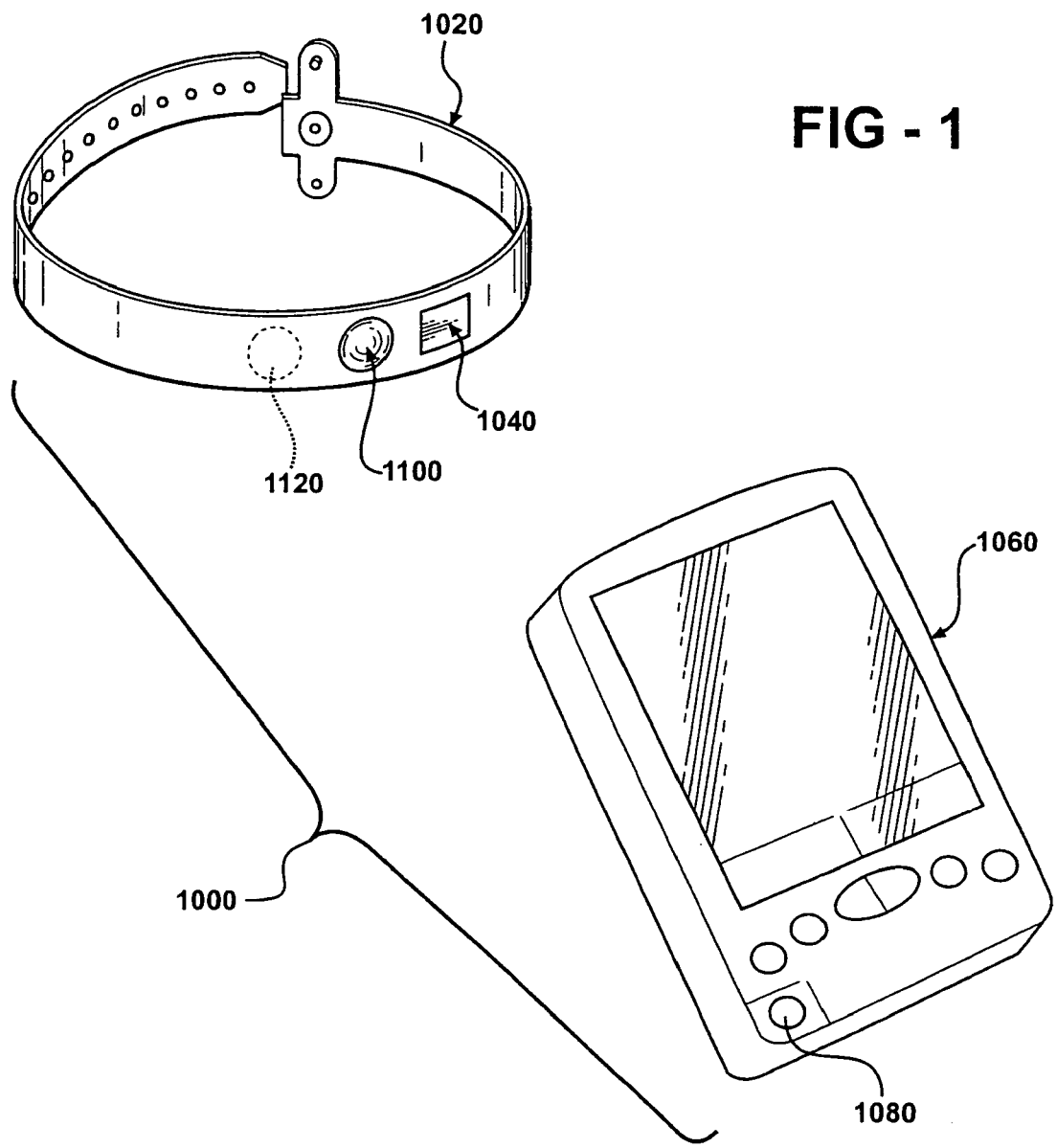
FIG. 1 is a drawing illustrating an embodiment of the invention.

A system for verifying patient identity is provided which allows hospital personnel to reduce error in patient care due to misidentification of a patient. Broadly, an inventive system for verifying patient identity includes a machine readable wireless tag containing identification information, the tag attached to an identification badge worn by a patient, a device having data input and output capacity, processing circuitry, memory circuitry and an executable program for analysis of data transmitted from the tag, and a machine readable wireless reader in data communication with the tag and the device. Also included is a signal display element for displaying a signal to a user, the signal display element disposed on the device or the reader. Optionally included is a status indicator disposed on the identification badge.

As used herein a machine readable wireless identification tag is defined to include a radio frequency identification (RFID) tag, one-dimensional or two-dimensional barcode.

Preferably, a plurality of identification badges are included in an inventive system, each badge having a machine readable wireless tag containing different identification information. The badges are distributed to a plurality of patients admitted or treated at a medical care facility or treatment locality. In a preferred embodiment, the plurality of badges are disposable, to be discarded once the patient is treated or released from the facility. However, optionally, badges are recovered to be reused.

An inventive system for verifying patient identity includes an identification badge configured to be worn by a patient or attached to clothing worn by the patient. In a preferred embodiment, the identification badge is configured as a wristband. A wristband badge for use in a medical care setting is an elongated flexible strip having at least an external surface of biocompatible material. Further, a wristband is provided with an attachment element in order to secure the wristband about the wrist of a patient. For example, an attachment element may be an adhesive coating on a portion of the wristband such that contact of the adhesive coating on the portion of the wristband with a second portion of the wristband secures the wristband to the patient's wrist. Other attachment elements for wristbands are known and may be used in securing a wristband included in an inventive system. For example, each end of the wristband may by configured so as to form an interlocking fastener, such as a buckle. It is understood that a badge configured as described for use as a wristband may also be produced in appropriate sizes in order to be secured to other body parts of the patient such as a finger, neck, leg, waist, ankle, or toe.

In other embodiments the identification badge wearable by a patient is configured to be affixed to an item of patient clothing. In an illustrative example, an identification badge may be affixed to an item of patient clothing by an adhesive or by a mechanical fastener.

A machine readable wireless tag is attached to the identification badge. For example, radio frequency tag circuitry may be layered between sheets of a sheet material such as paper or plastic. Further, tag circuitry may be printed or deposited on a portion of material incorporated in the badge.

As noted, a machine readable wireless tag attached to an identification badge included in an inventive system preferably contains identification information. For example, the tag contains information such as a patient identification number or code and/or a tag identifier unique within the system. The tag may further contain information regarding the patient to whom the badge is assigned.

Various types of machine readable wireless tag and reader combinations may be used in an inventive system and method. In one embodiment, the tags are passive RFID tags or barcodes, those that transmit information only in response to interrogation by a reader. In general, a passive RFID tag is energized to transmit identification information by the reader or a barcode scanned. Passive RFID tags may include an energy source, such as a battery, for example to increase read range. Such tags are often termed semi-passive or battery-assisted passive.

In another embodiment, the tags are active RFID tags and may initiate information transmission. Active tags are powered by an energy source, such as a battery, and may transmit continuously or intermittently. Thus, an identification badge including an attached active RFID tag may also include a power source, such as a battery, attached to the badge and in electrical communication with the tag. A preferred power source is a lightweight, inexpensive power source. Exemplary power sources include batteries and capacitors known in the art. One such power source is a paper capacitor described in U.S. Pat. No. 6,603,400.

Numerous radio frequency identification readers and tags have been developed illustratively including those described in U.S. Pat. Nos. 4,442,507; 4,796,074; 5,095,362; 5,296,722; 5,347,263; 5,347,280; 5,378,880; 5,407,851; 5,430,441; 5,528,222; 5,550,547; 5,521,601; 5,541,604; 5,565,846; 5,682,143; and 5,625,341.

In one embodiment, the radio frequency tags are read-only. Such tags are known in the art and are exemplified by the "ES600-Series Read Only Tags" commercially available from Escort Memory Systems (EMS), Scotts Valley, Calif. Alternatively, tags are configured to allow information to be written to the tag. For instance, the patient's name, address, hospital ID and/or medical information may be written to the RFID tags. Read-write tags are known in the art and include IntelliTag Series from Intermec Technologies Corporation and the HMS-100 Series passive read-write tags available from EMS.

Optionally, written information, including a written indicator of identification, such as an ID number, is affixed to the badge along with the tag.

A tag reader is included in an inventive system which is configured to interrogate the tag and receive identification information from the tag.

The reader is in data communication with a device having input and output capacity, processing and memory circuitry, along with an executable program for analysis of data transmitted from the tag. An included program is adapted to create, store and access a record of an association between tag information and patient data as described herein. An included program is further adapted to compare identification information transmitted by a tag with a retrieved record to determine if the transmitted identification information is associated with a specified patient.

Exemplary devices include a personal digital assistant, personal computer or mainframe computer. Optionally, the device is portable. The reader may be in wireless or direct wired connection to the device for communication of data. In addition, information received from the tag may be input from a reader over a wired or wireless connection to a device configured as a server or computer network accessible by multiple users from multiple locations. The server may be any type of computer system such as a personal digital assistant, personal computer, workstation or mainframe computer.

Optionally, a machine wireless reader is directly incorporated in a device including processing and memory circuitry as described above. Such devices illustratively include an RFID reader with database and processor components, a personal digital assistant having an RFID reader capability or personal computer having RFID reader capability and a barcode reader.

Input capacity of the device may be accessed by wireless or wired connection to an RFID reader as noted above. Input capacity of the device may be further accessed by wireless or wired connection to a user input apparatus for input to the device. A user input apparatus is any of various known in the art illustratively include a pushbutton, a touch-activated screen, a mouse, a keyboard and the like.

The tag includes identification information which is associated with the patient in a process for use of an inventive system. In general, the identification information included in and transmissible by the tag is associated with the patient upon arrival or admission to a hospital or medical treatment facility, including for instance, an ambulance. For example, a reader interrogates or scans an identification badge having an attached tag and receives identification information, such as an identification number or code unique within the system, from the tag. The identification information received by the reader is associated with patient data such as the patient's name, address, diagnosis, condition, date and time of admission, place of admission or the like. For instance, such association is achieved by input of patient data and tag identification information into the device included in an inventive system, the device having processing and memory circuitry along with a program executable by the circuitry to create and record an association between the data and the identification information, as well as to provide later access to the stored associated data.

A signal display element included in an inventive system is operative to present a user with a signal relating to a process implemented by a system of the present invention. In general, a display is activated in response to commands from device circuitry to present a signal to a user. A signal displayed by a signal display element is a visual or acoustic signal such as a text message, a light indicator, such as a colored and/or flashing light, and/or an acoustic signal, such as a warning tone. The display is preferably attached to the device and/or the reader, but may be a standalone display with wireless connection to the device and/or reader. A display illustratively includes a display screen, a light signal emitter, such as an LED, and an acoustic signal emitter.

A signal display element is operative to present a signal relating to a process implemented by a system such as positive or negative verification of the patient's identity, "reader interrogation transmitted," "pending verification," power supply to the reader, and the like.

In another embodiment, the signal display element is operative to present a first and a second signal to a user. Thus, a signal display element may present a first signal relating to a process of patient identity verification and a second signal relating to the process. For example, a blinking light is an example of a first signal relating to a process implemented by a system such as "reader interrogation transmitted," "pending verification" or the like. A continuous light emission from the first status indicator is an example of a second signal relating to a process implemented by a system indicating positive verification.

A second signal display element is optionally included attached to the reader and/or device. Thus, a first signal display element may present a first signal relating to a process implemented by a system of patient identity verification and a signal display element may present a second signal relating to the process. For example, a red light may be presented by a first signal display element as a signal relating to a process implemented by a system such as "reader interrogation transmitted," "pending verification" or the like. A green light may later be presented by a second signal display element as a signal indicative of positive verification of patient identity for instance.

A status indicator is optionally included in an inventive system which is operative to present a user with a cue relating to a process implemented by a system of the present invention. The status indicator is preferably attached to an identification badge. In general, a status indicator is activated in response to commands from device circuitry to present a cue to a user. In one embodiment, a status indicator is activated to present a cue in response to a transmitted signal from the reader. For instance, a reader transmitted signal may be received by an RFID tag antenna or a barcode optical sensor and further transmitted by tag circuitry in connection with a status indicator to activate the indicator.

In one embodiment of the invention, processing and memory circuitry is included attached to an identification badge along with a program executable by the circuitry to carry out a comparison of identification information transmitted to the identification badge with identification information stored in memory. In use, a radio frequency transmitter broadcasts a message including the patient identification information to the plurality of identification badges included in the system. Each badge receiving the message processes the identification information, comparing the broadcast patient identification information with stored patient identification information retrieved from the memory element. A match is indicated by activation of a status indicator to present a cue indicative of the match. Optionally, the processor is programmed to activate a status indicator to present a non-match signal by those badges which received the transmission but where the broadcast information did not match the stored information.

A cue displayed by a status indicator is a visual or acoustic cue such as a text message, a light indicator, such as a colored and/or flashing light, and/or an acoustic cue, such as a warning tone. In a preferred option, a power source is included in electrical communication with the status indicator disposed on an identification badge. Preferred is a lightweight, inexpensive power source such as a paper capacitor described in U.S. Pat. No. 6,603,400 or other such power sources. A display illustratively includes a display screen, a light signal emitter, such as an LED, and an acoustic signal emitter. A second status indicator operative to present a second cue is optionally included attached to the identification badge.

A status indicator is operative to present a cue relating to a process implemented by a system such as positive or negative verification of the patient's identity, "reader interrogation transmitted," "pending verification," power supply to the status indicator, and the like.

A cue presented by a status indicator is preferably a visual cue and/or an acoustic cue. For example, a status indicator is illustratively an indicator light such as an LED. Where the status indicator is a light indicator, the light is optionally a color indicator commonly associated with a positive or negative result. For example, a green light is preferably used where the cue is indicative of positive verification of patient identity, and a red light is preferably used where the cue is indicative of negative verification of patient identity. Further, a cue presented by the status indicator may be a blinking or continuous light emission. In an alternative embodiment, a status indicator is operative to present an acoustic cue such as a continuous or intermittent tone.

In another embodiment, the status indicator is further operative to present a first cue and a second cue to a user.

Thus, a status indicator may present a first cue indicative of a first status of a process of patient identity verification and a second cue indicative of a second status of the process. For example, a blinking light is an example of a first signal indicative of a status such as "reader interrogation transmitted," "pending verification" or the like. A continuous light emission from the status indicator may then indicate positive verification.

A second status indicator is optionally included attached to the identification badge. Thus, a first status indicator may present a first cue indicative of a first status of a process of patient identity verification and a second status indicator may present a second cue indicative of a second status of the process. For example, a red light may be presented by a first status indicator as a first cue indicative of a status such as "reader interrogation transmitted," "pending verification" or the like. A green light may be presented by a second status indicator as a second cue indicative positive verification of patient identity for instance.

In a preferred embodiment, activation of signals and cues are controlled by the device such that a signal and cue are synchronized.

In a preferred embodiment, an alert signal is presented to a user when more than one readable tag is within range of the reader.

In operation of an embodiment of an inventive system, a patient is provided with an identification badge having an attached machine readable wireless tag to a patient or to an article of the patient's clothing. The tag contains information associated with patient data in a device memory. A user inputs information to the device having data input and output capacity, processing circuitry, memory circuitry and an executable program for analysis of data transmitted from the tag, via a user input apparatus to indicate which patient's identity is to be verified. For instance, a user selects a patient indicator such as the patient's name, patient ID number, description or picture from a list displayed on a touch activated display screen. Selection of the patient indicator directs retrieval of a stored record of machine readable wireless identification information assigned to the patient. A provided machine readable wireless reader is activated to transmit an interrogation signal from the reader to the tag and, in response, identification information associated with the patient is transmitted from the tag to the reader. The identification information transmitted from the tag is compared with the retrieved record of the identification information assigned to the patient. Where the identification information transmitted from the tag matches the retrieved record of the identification information assigned to the patient, a signal display element is activated to present a signal indicative of verified patient identity. In the case of a mismatch between the identification information transmitted from the tag and the record, the signal display element is activated to present a negative verification signal.

In an embodiment in which a status indicator is included attached to the badge, the status indicator is activated to present a first cue or a first and second cue to a user. In a preferred embodiment, the first cue is identical to the first signal and the second cue is identical to the second signal, if present. Thus, for example, a first signal which is a "process pending" signal presented by the signal display element attached to the reader or device is identical to a "process pending" cue presented at about the same time by the status indicator attached to the badge. Further, where a first signal is a "patient identity verified" signal presented by the signal display element attached to the reader or device, an identical "patient identity verified" cue is presented at about the same time by the status indicator attached to the badge.

In another embodiment, the step of user indication of which patient's identity is to be verified by selecting an indicator of patient identity is omitted from the immediate process of verification as described above. For example, a reader dedicated to a patient may be provided. Such a reader may be programmed to compare identification information received from a tag only with patient data of a specified patient. Optionally, the patient's name or other identity indicator is continuously displayed on a dedicated reader. Further optionally, a dedicated reader may be attached to a structure or object associated with the patient's location, such as a bed, hospital room wall or the like.

FIG. 1 illustrates an embodiment of an inventive system for verifying patient identity 1000 which includes an identification badge 1020 to be worn by a patient. The badge has a radio frequency identification tag 1040 attached to the badge 1020 and the tag 1040 has associated identification information which is assigned to the patient. An illustrated system further includes a radio frequency reader integrated in a device 1060 having data input and output capacity, processing circuitry, memory circuitry and an executable program for analysis of data transmitted from the tag. An inventive system also includes a signal display element 1080 in electrical communication with the device 1060, the signal display element 1080 operative to present to a user a first signal. Optionally a status indicator 1100 is attached to the identification badge 1020. Further optionally a power source 1120 is connected to the tag and/or the status indicator is housed by the identification badge. The device 1060 is powered by conventional means such as a battery or connection to AC.

In a further embodiment of an inventive system, an alert is included for alerting hospital personnel to presence of an object or person having a radio frequency identification tag not associated with a first patient in proximity to the first patient. In one embodiment, a reader is fixed in location such that a physical area in the read range of the reader is designated as assigned to the first patient. Such an embodiment of the invention allows for controlled access to the first patient and provides a warning or alert when a person or object associated with a second patient is close to the first patient so that measures may be taken to prevent erroneous treatment.

Broadly, an inventive system includes at least two identification badges, each having an attached machine readable wireless tag containing identification information as described herein. A reader is provided along with a device having data input and output capacity, processing circuitry, memory circuitry and an executable program for analysis of data transmitted from a tag as described herein. In a preferred option, the reader is fixed in location to define an area associated with the patient. Also included is a signal display for alerting hospital personnel to presence of an object or person having a radio frequency identification tag not associated with a patient in proximity to the patient.

Each patient in a care unit, such as a hospital or emergency room, has identification information stored in and transmissible by a machine readable wireless tag attached to the patient. The identification information is associated with patient data in memory contained in or accessible by the described device. Further, other objects are associated with the patient by attachment of a machine readable wireless tag containing identification information associated with patient data in the memory.

An identification badge is generally attached to a patient upon admission to a medical care facility such as a hospital or clinic and identification information included in the tag attached to the badge is input to a device memory along with patient data such as the patient's name, address, picture, diagnosis, condition and the like. The identification information and patient data are associated as described herein. Further, certain objects in addition to the identification badge may be defined as associated with the patient by attachment of a second machine readable wireless tag containing identification information associated with the patient data. Such association may be achieved by writing information indicative of an association to the tag in an embodiment in which the tag is a read-write tag. For instance, a patient identification number or identification information related to identification information contained in the identification badge may be written to the tag.

The degree of proximity which is tolerated before an alert is triggered may be established in various ways. In a preferred system, the degree of proximity tolerated is established by the read range of the tags. The read range of a tag is determined by various factors, including whether the tags included in the system are passive or active. Another major consideration is the frequency at which the system operates. For example, a system operating in the lower frequency range, such as 13.56 MHz, has a shorter read range than one operating at 433 MHz. In general, RFID tags have a read range of about 5 feet or less. However, some tags have a read range of nearly 250 feet. Thus, in one embodiment an area of a treatment facility is designated as specific to a first patient by establishing a fixed reader at a location in proximity to the patient. Preferably, the reader is located where a tagged object for use in treating the patient will be detected by the reader. For example, a reader may be affixed to the patient's bed, a wall in a treatment bay, an incubator, or other fixture in a patient's room or treatment area.

In one embodiment, the tags included in an inventive system are active tags and a power source is included in electrical connection with these tags. In such an embodiment, the tags are configured to continuously or intermittently emit a signal containing identification information receivable by the reader.

In a further embodiment, the reader is configured to continuously or intermittently transmit an interrogation signal and to receive a response from tags within the read range. Such responses are subjected to analysis to determine if a tag not associated with the patient in the designated patient area is present.

In a further example, identification information contained in the tag may be read and input to the processing and memory circuitry of the device for association with patient data in a process analogous to that described for the initial association of the identification badge tag identification information with patient data. For example, a physician may order administration of a drug for treatment of a patient. The tag having identification information is attached to the drug container. The identification information contained by the tag is associated with the patient for whom the drug is ordered. Tags are preferably attached to other objects to assure that the object is intended for treatment of the patient or use by the patient, such as medication containers, specimen containers, meal trays, and the like.

In a preferred option, a radio frequency identification reader is stationed in proximity to the patient in order to establish an area of a facility specifically designated for a particular patient. For example, a hospital room, emergency room bay, operating room or the like may be specifically designated for use of the patient such that a tag having identification information not associated with the patient results in activation of a signal indicative of that fact.

Figure 2:
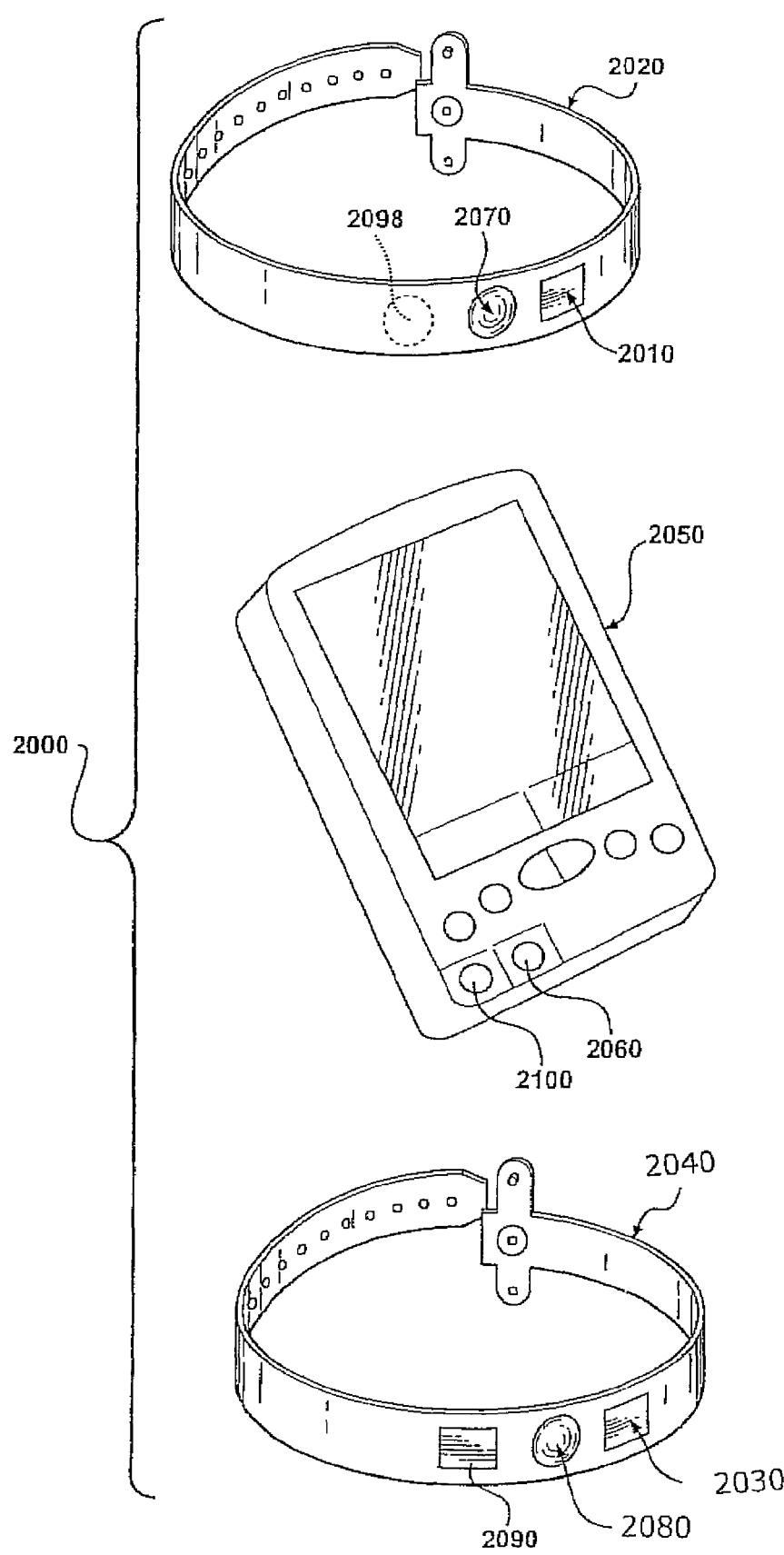
FIG. 2 is a drawing illustrating an embodiment of the invention.

FIG. 2 depicts a radio frequency identification system 2000 for alerting hospital personnel to presence of an object or person having a radio frequency identification tag not associated with a target patient in an area designated for use by the target patient. In the illustrated embodiment a first radio frequency tag 2010 containing identification information specific to a target patient is attached to an identification badge 2020 to be worn by the target patient or to an object associated with the target patient. A second radio frequency tag 2030 containing identification information specific to a non-target patient is attached to an identification badge 2040 to be worn by the non-target patient or to an object associated with the non-target patient. An illustrated embodiment of an inventive system further includes a radio frequency reader 2050 containing a target patient identification record, the reader operative to transmit a signal receivable by each of said first and second tags, the reader operative to receive an identification signal from each of said first and second tags, and the reader further operative to compare the identification signal received from the first and second tags with the identification information specific to the target patient and to determine whether each of the first and second identification signals is associated with the identification information specific to the target patient. The illustrated system further includes a signaling device 2060 in communication with the reader, the signaling device operative to provide a signal indicative of presence of a tag associated with a non-target patient in an area designated for use by the target patient. Further a system optionally includes a second signaling device 2070, the second signaling device attached to the identification badge 2020 as shown or to a target patient associated object other than the badge. A third signaling device 2080 is optionally included attached to the non-target patient identification badge. This signaling device is optionally configured to display a signal indicative of the fact that the person wearing the badge is the non-target patient. Target and non-target patient identification badges, 2020 and 2040 respectively, optionally include a power source shown at 2090 and 2098 respectively. In a further option, a further signaling device 2100 is optionally attached to the reader 2050.

While this application describes embodiments of the invention as including a radio frequency transponder or tag, it is appreciated that devices using other signal types are operative in embodiments of the present invention. For example, infrared reader/tag combinations may be used.

Any patents or publications mentioned in this specification are herein incorporated by reference to the same extent as if each individual publication was specifically and individually indicated to be incorporated by reference. In particular, applications for U.S. patent entitled "Associated Patient Care Items" and "Modular Hospital Cart," both filed Jan. 21, 2005, are hereby incorporated by reference in their entirety.

One skilled in the art will readily appreciate that the present invention is well adapted to carry out the objects and obtain the ends and advantages mentioned, as well as those inherent therein. The apparatus and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:
1. A system for verifying patient identity, comprising:
an identification badge to be worn by a patient, the identification badge comprising a machine readable wireless identification tag; the tag having a tag circuitry and containing identification information, the tag circuitry having processing circuitry and memory circuitry;

a device having data input and output capacity, processing circuitry, memory circuitry and a first executable program for analysis of data transmitted from the tag;

a machine readable wireless reader in data communication with the tag and the device;

a signal display indicator disposed on the reader or the device, the signal display indicator operative to display a first signal in response to a command by the first executable program, the first signal indicative of a pending process, or verified or non-verified patient identity;

a second executable program executable by the tag circuitry and operative to compare stored patient identification information transmitted to the tag with the identification information contained in the tag in order to determine whether the stored patient identification information transmitted to the tag matches the identification information contained in the tag; and a status indicator attached to the identification badge and in communication with the tag via the tag circuitry, the status indicator operative to present a first cue confirming positive or negative verification of the patient's identity.

2. The system of claim 1 wherein the identification badge is a wristband.

3. The system of claim 1 wherein the first signal is selected from a group consisting of: a visual signal and an acoustic signal.

4. The system of claim 1 wherein the signal display indicator is further operative to present a second signal of the process status of the verifying of patient identity.

5. The system of claim 1 further comprising a power source attached to the identification badge and in electrical communication with the status indicator.

6. The system of claim 1 wherein the first cue is selected from a group consisting of: visual and acoustic.

7. The system of claim 1 wherein the reader is disposed on the device.

8. The system of claim 1 wherein the tag is an RFID tag of a type selected from a group consisting of: passive, active, read-only and read-write.

9. The system of claim 1 wherein the device is selected from a group consisting of: a personal digital assistant, a personal computer a mainframe and a server.

* * * * *